US012569186B2

(12) United States Patent
Sadeghi et al.

(10) Patent No.: US 12,569,186 B2
(45) Date of Patent: Mar. 10, 2026

(54) APPARATUS AND METHOD FOR AUGMENTED INTERPRETATION OF MAGNETIC RESONANCE AND ULTRASOUND SHEAR WAVE ELASTOGRAPHY FOR MONITORING LIVER FIBROSIS

(71) Applicant: KONINKLIJKE PHILIPS N.V., Eindhoven (NL)

(72) Inventors: Seyedali Sadeghi, Melrose, MA (US); Claudia Errico, Medford, MA (US); Jochen Kruecker, Andover, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 150 days.

(21) Appl. No.: 18/273,127

(22) PCT Filed: Jan. 25, 2022

(86) PCT No.: PCT/EP2022/051522
§ 371 (c)(1),
(2) Date: Jul. 19, 2023

(87) PCT Pub. No.: WO2022/161915
PCT Pub. Date: Aug. 4, 2022

(65) Prior Publication Data
US 2024/0090823 A1     Mar. 21, 2024

Related U.S. Application Data

(60) Provisional application No. 63/142,024, filed on Jan. 27, 2021.

(51) Int. Cl.
*A61B 5/00*      (2006.01)
*A61B 5/055*      (2006.01)
*A61B 8/00*      (2006.01)

(52) U.S. Cl.
CPC ............ *A61B 5/4244* (2013.01); *A61B 5/055* (2013.01); *A61B 5/7267* (2013.01); *A61B 8/463* (2013.01); *A61B 8/465* (2013.01); *A61B 8/5223* (2013.01)

(58) Field of Classification Search
CPC ..... A61B 5/4244; A61B 5/055; A61B 5/7267; A61B 8/463; A61B 8/465; A61B 8/5223;
(Continued)

(56) References Cited

U.S. PATENT DOCUMENTS

| 6,508,768 B1 * | 1/2003 | Hall | .................... | G01S 7/52061 600/443 |
| 6,558,324 B1 * | 5/2003 | Von Behren | ............. | A61B 8/08 600/443 |

(Continued)

FOREIGN PATENT DOCUMENTS

WO          2020261205 A1     12/2020

OTHER PUBLICATIONS

International Search Report and Written Opinion for PCT/EP2022/051522; Mailing date: May 3, 2022, 10 pages.
(Continued)

*Primary Examiner* — Sanjay Cattungal

(57) ABSTRACT

A method and system (100) for augmented interpretation of shear wave elastography between first and second imaging modalities comprises performing an elastography measurement via a second imaging modality (20), different from a first imaging modality (10), to obtain at least one second imaging modality elastography value (32, 60) of a region of interest (33). At least one corresponding first imaging modality elastography value (36, 38, 62) is predicted based on the obtained second imaging modality elastography value. A graphical user interface or smart report dashboard (50) is generated that shows (i) a fibrosis level (521) of the
(Continued)

| Normal | Normal or chronic | Stage 1-2 | Stage 2-3 | Stage 3-4 | Stage 4 | region of interest, wherein the fibrosis level is determined as a function of (i)(a) the at least one second imaging modality elastography value (32) and/or (i)(b) the predicted at least one corresponding first imaging modality elastography value (36, 38).

20 Claims, 17 Drawing Sheets

(58) Field of Classification Search
CPC ....... A61B 2576/02; A61B 8/08; A61B 8/461; A61B 8/485; G01R 33/5608; G01R 33/4814; G01R 33/56358
See application file for complete search history.

(56) References Cited

U.S. PATENT DOCUMENTS

| | | | | |
|---|---|---|---|---|
| 8,469,891 | B2 * | 6/2013 | Maleke | A61B 5/055 |
| | | | | 73/602 |
| 9,066,679 | B2 * | 6/2015 | Beach | A61B 8/08 |
| 9,603,583 | B2 * | 3/2017 | Choi | A61B 8/485 |
| 9,726,647 | B2 * | 8/2017 | Walker | G01N 29/4472 |
| 10,342,514 | B2 * | 7/2019 | Kanayama | A61B 8/5207 |
| 2009/0056453 | A1 * | 3/2009 | McAleavey | A61B 8/5207 |
| | | | | 73/597 |
| 2009/0270730 | A1 * | 10/2009 | Azuma | G01S 7/52042 |
| | | | | 600/443 |
| 2009/0292205 | A1 * | 11/2009 | Osaka | G01S 7/52042 |
| | | | | 600/443 |
| 2009/0304246 | A1 * | 12/2009 | Walker | G01S 15/8979 |
| | | | | 382/128 |
| 2011/0263978 | A1 * | 10/2011 | Chen | A61B 8/485 |
| | | | | 600/438 |
| 2013/0102932 | A1 * | 4/2013 | Cain | A61N 7/02 |
| | | | | 601/2 |
| 2013/0211253 | A1 * | 8/2013 | Hsu | A61B 8/485 |
| | | | | 600/438 |
| 2013/0218012 | A1 * | 8/2013 | Specht | A61B 8/4444 |
| | | | | 367/7 |
| 2014/0064021 | A1 * | 3/2014 | Nagae | G01S 7/52047 |
| | | | | 367/7 |
| 2014/0064022 | A1 * | 3/2014 | Nagae | G01S 7/52046 |
| | | | | 367/7 |
| 2014/0064023 | A1 * | 3/2014 | Nagae | G01S 7/52063 |
| | | | | 367/7 |
| 2014/0276058 | A1 * | 9/2014 | Fan | A61B 5/4872 |
| | | | | 600/442 |
| 2014/0330122 | A1 * | 11/2014 | Baghani | A61B 8/463 |
| | | | | 600/438 |
| 2015/0133783 | A1 * | 5/2015 | Tabaru | A61B 8/485 |
| | | | | 600/438 |
| 2015/0148658 | A1 * | 5/2015 | Smith | A61B 8/485 |
| | | | | 600/443 |
| 2015/0148673 | A1 * | 5/2015 | Yoshikawa | A61B 8/5207 |
| | | | | 600/438 |
| 2015/0164476 | A1 * | 6/2015 | Kong | G01S 7/52022 |
| | | | | 600/438 |
| 2015/0182122 | A1 * | 7/2015 | Bamber | G01S 7/52022 |
| | | | | 600/407 |
| 2015/0192547 | A1 * | 7/2015 | Lee | A61B 8/06 |
| | | | | 73/641 |
| 2015/0272547 | A1 * | 10/2015 | Freiburger | A61B 8/52 |
| | | | | 600/438 |
| 2015/0320394 | A1 * | 11/2015 | Arnal | A61B 8/485 |
| | | | | 600/438 |
| 2016/0089113 | A1 * | 3/2016 | Choi | G01S 15/892 |
| | | | | 600/438 |
| 2016/0128674 | A1 * | 5/2016 | Shin | A61B 6/5247 |
| | | | | 600/436 |
| 2016/0327525 | A1 * | 11/2016 | Li | A61B 8/485 |
| 2017/0112471 | A1 * | 4/2017 | Toji | A61B 8/4254 |
| 2017/0340310 | A1 * | 11/2017 | Carlini | G01S 7/52085 |
| 2017/0347990 | A1 * | 12/2017 | Watanabe | G01S 7/52022 |
| 2017/0360408 | A1 * | 12/2017 | Toji | G01S 7/52017 |
| 2018/0296190 | A1 * | 10/2018 | Susumu | A61B 8/5269 |
| 2019/0183461 | A1 * | 6/2019 | Sonoyama | G01S 7/52042 |
| 2020/0060654 | A1 * | 2/2020 | Nguyen | G01S 7/52042 |
| 2022/0401073 | A1 * | 12/2022 | Konofagou | A61B 8/5223 |
| 2023/0044531 | A1 * | 2/2023 | Etaix | G01N 29/07 |

OTHER PUBLICATIONS

Audière, S. et al., "Maximum Likelihood Estimation of Shear Wave Speed in Transient Elastography", IEEE Transactions on Medical Imaging, 2014, vol. 33, No. 6, pp. 1338-1349.

Godfrey, E.M. et al., "Magnetic Resonance Elastography in the Diagnosis of Hepatic Fibrosis", Seminars in Ultrasound, CT and MRI, 2013, vol. 34, Issue 1, pp. 81-88.

Li, H. et al., "Deep learning in ultrasound elastography imaging: A review", Medical Physics, 2022, vol. 49, Issue 9, pp. 5993-6018.

Wildeboe, R. R. et al., "Synthetic Elastography Using B-Mode Ultrasound Through a Deep Fully Convolutional Neural Network", IEEE Transactions on Ultrasonics, Ferroelectrics, and Frequency Control, 2020, vol. 67, No. 12, pp. 2640-2648.

Bataller, R. et al., "Liver Fibrosis", J Clin Invest., 2005, vol. 115, No. 2, pp. 209-218.

Liang, Y. et al., "Magnetic resonance elastography in staging liver fibrosis in non-alcoholic fatty liver disease: a pooled analysis of the diagnostic accuracy", BMC Gastroenterol., 2020, vol. 20, 12 pages.

Sadeghi, S. et al., "Narrowband Shear Wave Generation Using Sinusoidally Modulated Acoustic Radiation Force", IEEE Transactions on Ultrasonics, Ferroelectrics, and Frequency Control, 2019, vol. 66, No. 2, pp. 264-272.

Toguchi, M. et al., "Magnetic resonance elastography in the assessment of hepatic fibrosis: a study comparing transient elastography and histological data in the same patients", Abdom Radiol., 2017, vol. 42, pp. 1659-1666.

Hsu, C. et al., "Magnetic Resonance vs Transient Elastography Analysis of Patients With Nonalcoholic Fatty Liver Disease: A Systematic Review and Pooled Analysis of Individual Participants", Clinical Gastroenterology and Hepatology, 2019, vol. 17, Issue 4, pp. 630-637.e8.

* cited by examiner

UE map

36

38

MRE
stiffness
value

Output: MRE map

Input: UE stiffness map

50

| Name: | John Doe |
| Accession no: | 0123456 |
| Referring physician: | Jane Healer, MD |

Procedure: ultrasound elastography exam
Vendor name (MRE/UE)
Prior exam: 10/03/2019
Current exam: 04/02/2020

68

Finding: 55% decrease in fibrosis stiffness

APPARATUS AND METHOD FOR AUGMENTED INTERPRETATION OF MAGNETIC RESONANCE AND ULTRASOUND SHEAR WAVE ELASTOGRAPHY FOR MONITORING LIVER FIBROSIS

CROSS-REFERENCE TO PRIOR APPLICATIONS

This application is the U.S. National Phase application under 35 U.S.C. § 371 of International Application No. PCT/EP2022/051522, filed on Jan. 25, 2022, which claims the benefit of U.S. Provisional Patent Application No. 63/142,024, filed on Jan. 27, 2021. These applications are hereby incorporated by reference herein.

BACKGROUND

The present embodiments relate generally to elastography and more particularly, to an apparatus for augmented interpretation of magnetic resonance and ultrasound shear wave elastography for monitoring liver fibrosis and a method thereof.

Liver disease is the twelfth leading cause of death in the United States. Various aetiologies of liver disease such as hepatitis B, hepatitis C, and nonalcoholic fatty liver disease (NAFLD) cause scarring in the liver. If the scarring remains untreated, it can lead to liver fibrosis, an advanced stage of liver disease. Liver fibrosis results from chronic damage to the liver in conjunction with the accumulation of extracellular matrix proteins. If left untreated, fibrosis can further advance to liver cirrhosis, liver cancer, liver failure, and death. Hence, it is critically important to diagnose and monitor liver fibrosis accurately.

The current gold standard for liver fibrosis diagnosis is liver biopsy, but there are several limitations associated with biopsy. A liver biopsy is invasive, and it causes anxiety. In some extreme cases, complications such as bleeding and liver rupture following biopsy may lead to death for patients who have comorbidities. Therefore, developing a non-invasive and accurate measurement tool for liver fibrosis assessment and treatment monitoring for better patient management is desirable.

Shear wave elastography has shown to be a promising tool to non-invasively measure the stiffness of soft tissues. Ultrasound shear wave elastography (UE) and magnetic resonance shear wave elastography (MRE) are both quantitative imaging techniques for diagnosing and monitoring liver fibrosis. With now reference to FIG. 1, a high-level system setup overview of a system for magnetic resonance shear wave elastography 10 is illustrated. For MRE, a patient is placed on a platform of the MRI scanner 12. A passive driver/transducer 14 is positioned on the patient with regard to a region of interest 16. The patient is then constrained within the MRI scanner during performance of the elastography measurement. In addition, with respect to MRE, a continuous acoustic vibration at low frequency (~60 Hz for liver) is transmitted into the region of interest (e.g., abdomen) of a subject using the passive driver, producing harmonic waves with a narrow frequency bandwidth, which means that the wave energy is concentrated at the desired frequency. Examples of six different stiffness maps (collectively designated by reference numeral 18), obtained via MRE with corresponding designations of fibrosis stage, are illustrated at the bottom of FIG. 1. Viewing the MRE stiffness maps, from left to right in FIG. 1 (i.e., with increasing levels of fibrosis), the respective fibrosis stage designations include F0: normal (no fibrosis); F1: portal fibrosis without septa; F2: portal fibrosis with rare septa; F3: numerous septa without cirrhosis; F4: cirrhosis.

Turning now to FIG. 2, a system setup overview of a system for ultrasound shear wave elastography 20 is illustrated. UE methods, which differ from MRE methods, use high-intensity short-duration ultrasound "push" pulses to generate a shear wave with a broad frequency spectrum. At the excitation step of the UE methods, it is difficult to accurately control how the energy of the wave is distributed within that broad frequency spectrum. One example of a stiffness map (designated by reference numeral 22) obtained via UE, with a corresponding color-coded stiffness scale 24 in the upper right-hand portion of the stiffness map, is also illustrated in FIG. 2.

Ultrasound imaging vendors use time-of-flight methods to reconstruct a shear wave speed, similar to the group velocity, out of a broad bandwidth, which is also vendor dependent. Because of the differences in shear wave frequency, the chosen tissue visco-elastic mechanical model and time delay estimation method, the shear-wave group-like velocity (m/s) and the subsequent stiffness value (kPa) reported by ultrasound systems do not match the velocity or stiffness value (kPa) measured by MRE. These differences render MRE and UE stiffness measurement non-interchangeable and, as a result, it is difficult to directly compare measurements obtained with UE and MRE.

No guidelines are known to have been proposed by any international clinical organizations on which elastography method (UE or MRE) to choose for diagnosis and monitoring of liver fibrosis. MRE is highly reproducible in healthy individuals and patients with liver fibrosis. In addition, MRE has a higher success rate than UE in diagnosing liver fibrosis (93% for MRE vs. 82% for UE). Furthermore, MRE has a more robust quantification performance, i.e., due to its higher shear wave SNR, 3D volume imaging, and by assessing a larger proportion of the liver, which may reduce sampling variability. However, MRE has some limitations. Additional time is required for positioning the passive driver, and the transducer causes discomfort in some patients.

Compared to MRE, UE is less expensive, faster, highly portable, and widely available, and it has been independently validated in numerous clinical centers worldwide. There are also clinical sites that do not have access to MRI scanners, and some patients prefer not to undergo MRE, again due to being constrained in the MR scanner. In these cases, UE is preferred over MRE during the monitoring phase for liver fibrosis due to the higher clinical value. Therefore, depending on the availability of the systems at clinical institutes, patient comfort level, and cost of care, MRE or UE is preferred for diagnosis and monitoring of liver fibrosis.

Although MRE and UE are both used for liver fibrosis diagnosis, due to the aforementioned technical differences between MRE and UE, the use of the same image modality is preferred for monitoring and consistency of measurements over time for a given patient. Using the same image modality ensures that the stiffness changes over time are only pathologic and due to patient-related factors, not to technical differences between MRE and UE (excitation frequency, instrument-related dependency, and post-processing algorithms). However, MRE is expensive, and performing MRE measurements at several time points or follow-up exams for liver monitoring puts a significant financial burden on the patient. Given the lower cost and broader availability of UE compared to MRE, it is desirable to use UE for the follow-up liver fibrosis monitoring. Also, some paediatric and elderly patients may feel discomfort in the MM scan, which could make the MRE exam more challenging and time-consuming (i.e., a lot of motion and repeated measurements).

Accordingly, an improved method and apparatus for overcoming the problems in the art are desired. It would further be desirable to provide a non-invasive and accurate measurement tool for liver fibrosis assessment and treatment monitoring for better patient management, and to remove a dependency on one imaging modality.

SUMMARY

In accordance with one aspect, the embodiments of the present disclosure bridge the gap between MRE and UE for monitoring liver fibrosis by 1) predicting a corresponding MRE stiffness value and confidence level (or score) by only performing an UE measurement and 2) providing a smart dashboard showing the fibrosis stage, confidence score, changes in stiffness value on a plot and table along with the stiffness maps of the original and predicted liver fibrosis.

According to one embodiment, a method for augmented interpretation of shear wave elastography between first and second imaging modalities comprises performing an elastography measurement via a second imaging modality, different from a first imaging modality, to obtain at least one second imaging modality elastography value of a region of interest. The method further comprises predicting, via a processor, at least one corresponding first imaging modality elastography value based only on the obtained second imaging modality elastography value. Subsequent to predicting, the method comprises generating, via the processor and a display, a graphical user interface or smart report dashboard that includes or shows (i) a fibrosis level of the region of interest, wherein the fibrosis level is determined as a function of (i)(a) the at least one second imaging modality elastography value and/or (i)(b) the predicted at least one corresponding first imaging modality elastography value.

In one embodiment, the second imaging modality is selected between (i) magnetic resonance shear wave elastography (MRE) and (ii) ultrasound shear wave elastography (UE). The first imaging modality comprises the non-selected imaging modality of the second imaging modality. The elastography values obtained via the second imaging modality are not comparable with elastography values obtained via the first imaging modality due to technical differences in excitation frequency and post-processing algorithms of each respective imaging modality.

According to an embodiment, the at least one second imaging modality elastography value and the at least one corresponding predicted first imaging modality elastography value each comprise one or more of (i) a stiffness map and (ii) a stiffness value in units of kPa. For example, the stiffness value comprises an average value of a respective stiffness map. In another embodiment, the method includes predicting a confidence score related to the at least one second imaging modality elastography value, wherein the predicted confidence score comprises a highest percentage of confidence among percentages of confidence in each of multiple fibrosis levels F0-F4 based on the second imaging modality elastography measurement; and selecting, via the processor, a predicted fibrosis level based on the fibrosis level having the highest percentage of confidence.

According to yet another embodiment, the smart report dashboard further includes (or shows) (ii) a baseline fibrosis level of the region of interest. The baseline fibrosis level is determined based on an initial baseline elastography measurement performed via the first imaging modality to obtain at least one baseline first imaging modality elastography value of the region of interest. In one embodiment, the baseline elastography measurement is performed prior to the elastography measurement via the second imaging modality. In yet another embodiment, the smart report dashboard further includes (or shows) (iii) a percentage change in elastography value between (iii)(a) the predicted at least one first imaging modality elastography value based on the obtained at least one second imaging modality elastography value and (iii)(b) the at least one baseline first imaging modality elastography value. In addition, the smart report dashboard further includes (shows) (iv) the at least one second imaging modality elastography value of the region of interest, (v) the predicted at least one corresponding first imaging modality elastography value of the region of interest, and (vi) a confidence score related to the at least one second imaging modality elastography value. The confidence score is a percentage between 0 and 100 percent and is representative of a level of confidence in the fibrosis level that is based on the at least one second imaging modality elastography value.

In one embodiment, predicting the at least one corresponding first imaging modality elastography value comprises initiating a deep learning-based algorithm to predict the at least one corresponding first imaging modality elastography value. The deep learning-based algorithm comprises a generative adversarial network (GAN) and/or a convolutional neural network (CNN). In another embodiment, the method further includes determining, via the processor and a second deep learning-based algorithm, a confidence score related to the at least one second imaging modality elastography value. Determining of the confidence score is automatically activated simultaneously with the initiating of the deep learning-based algorithm. The confidence score is further for providing a real-time classification of, or a level of confidence in, the fibrosis level that is based on the at least one second imaging modality elastography value.

According to another embodiment, a system for augmented interpretation of shear wave elastography between first and second imaging modalities comprises an input for receiving imaging data pertaining to an elastography measurement obtained from a second imaging modality, and a controller configured to perform an elastography measurement via the second imaging modality, different from a first imaging modality, to obtain at least one second imaging modality elastography value of a region of interest. The controller is further configured to predict at least one corresponding first imaging modality elastography value based only on the obtained second imaging modality elastography value. Subsequent to predicting, the controller is further configured to generate a graphical user interface or smart report dashboard that includes (or shows) (i) a fibrosis level of the region of interest, wherein the fibrosis level is determined as a function of (i)(a) the at least one second imaging modality elastography value and/or (i)(b) the predicted at least one corresponding first imaging modality elastography value. The system further comprises a display in communication with the controller to display the smart report dashboard.

Still further advantages and benefits will become apparent to those of ordinary skill in the art upon reading and understanding the following detailed description.

BRIEF DESCRIPTION OF THE DRAWINGS

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

DETAILED DESCRIPTION

Figure 1:
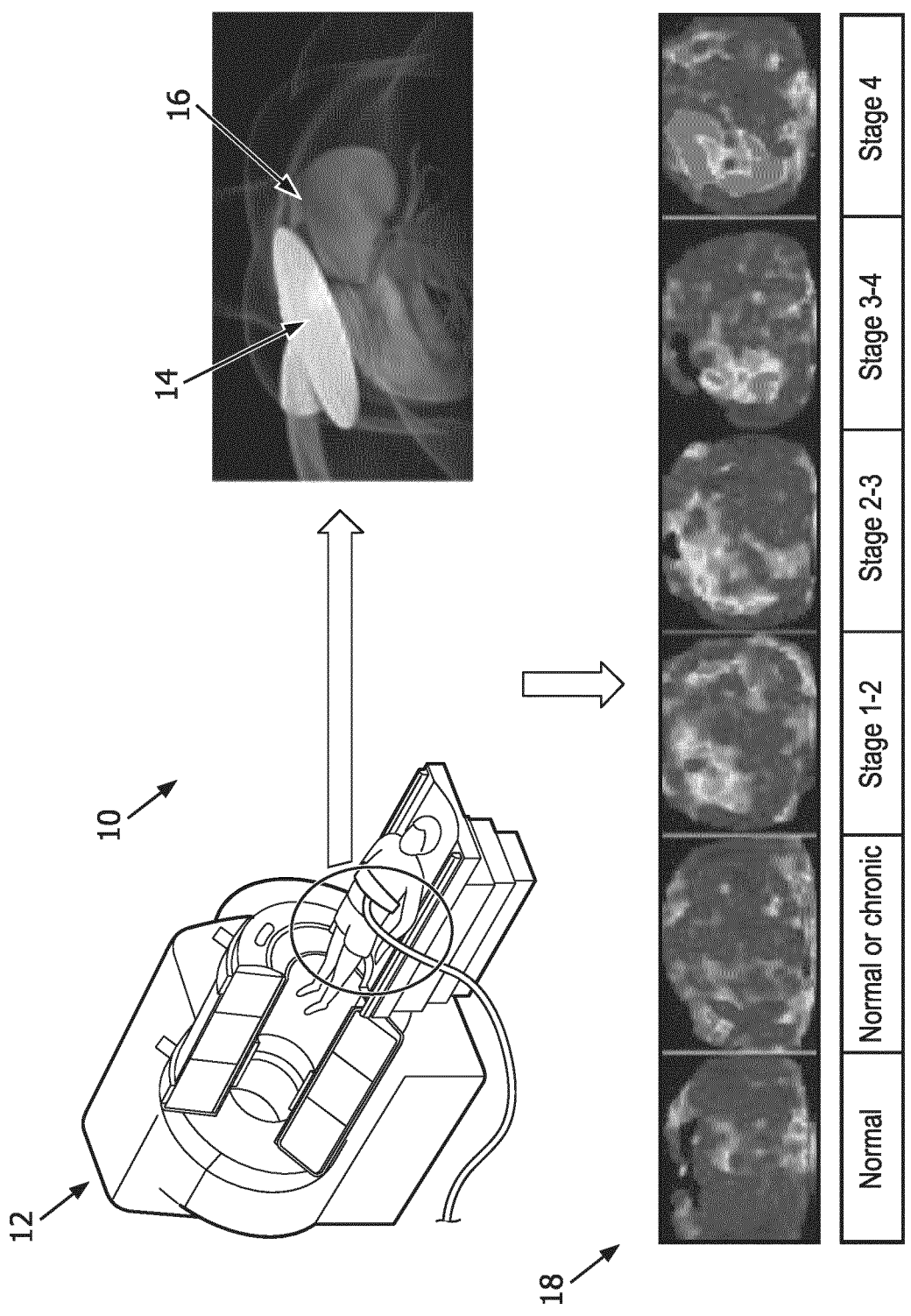
FIG. 1 is an illustrative flow-diagram view of a method for magnetic resonance shear wave elastography (MRE)

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 3:
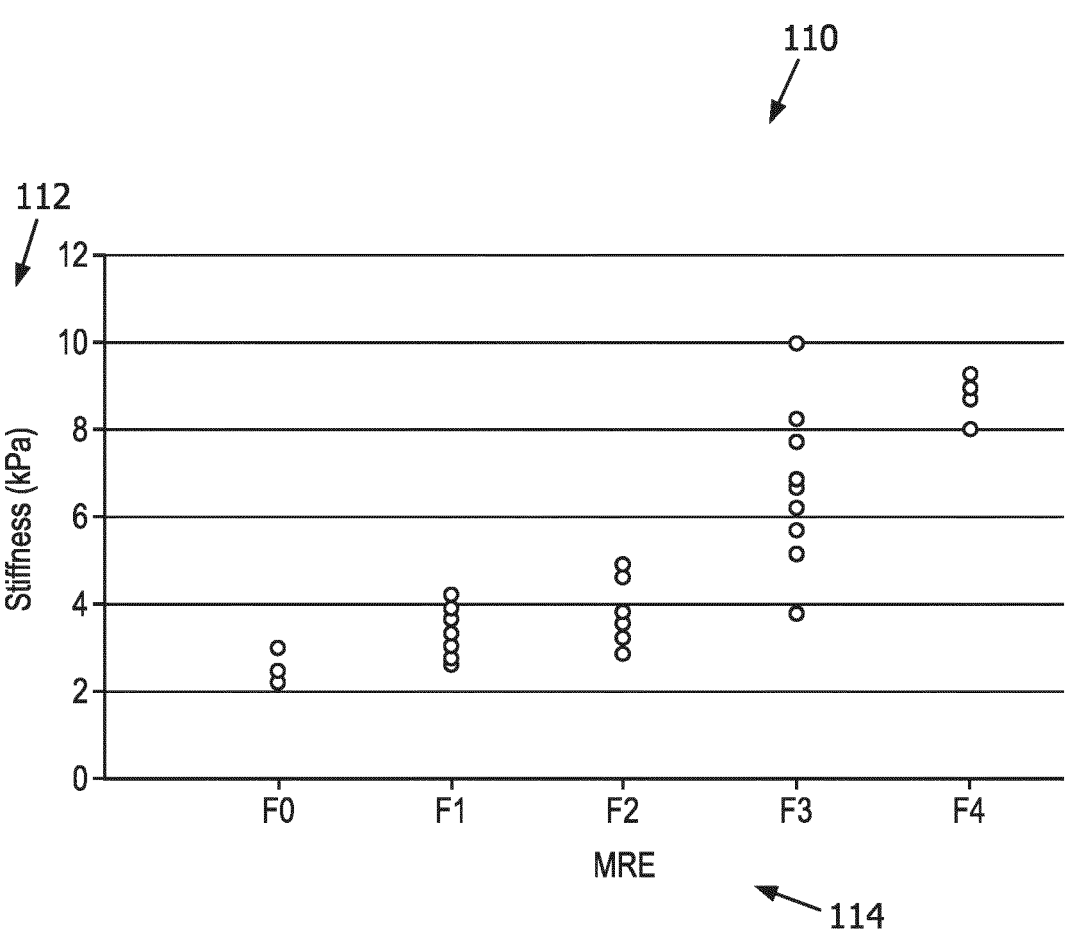
FIG. 3 is a graphical illustration indicating shear modulus (i.e., stiffness) obtained by MRE.
Figure 4:
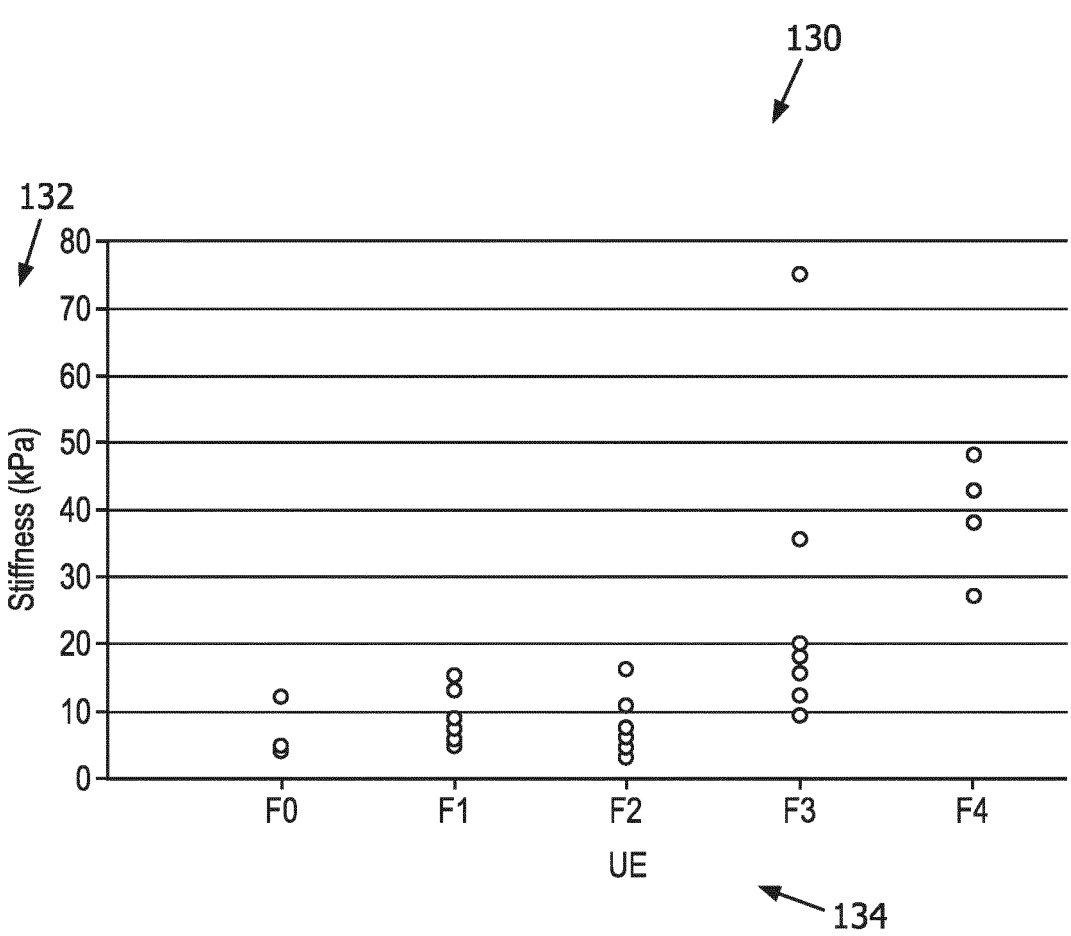
FIG. 4 is a graphical illustration indicating shear modulus obtained by UE.

To more fully appreciate the embodiments of the present disclosure, we first consider at least two problems/limitations known in the art which are overcome by the embodiments, as discussed herein below. With respect to a first problem, while there exist stiffness cut-off values in UE and MRE for liver fibrosis staging derived from liver biopsy as ground truth, the stiffness values in MRE and UE on the same patient are not comparable. For example, FIG. 3, illustrates a plot 110 of stiffness (kPa) versus liver fibrosis levels (F0, F1, F2, F3, and F4) for magnetic resonance shear wave elastography, MRE. With respect to plot 110, the left-hand vertical scale 112 comprises a stiffness scale for the first imaging modality in units of kPa and the horizontal scale 114 comprises a fibrosis level scale for the first imaging modality, from F0 to F4. FIG. 4, illustrates a plot 130 of stiffness (kPa) versus liver fibrosis levels (F0, F1, F2, F3, and F4) for ultrasound shear wave elastography, UE. With respect to plot 130, the left-hand vertical scale 132 comprises a stiffness scale for the second imaging modality in units of kPa and the horizontal scale 134 comprises a fibrosis level scale for the second imaging modality, from F0 to F4. The underlying reasons for the difference in stiffness values between MRE and UE include (i) technical differences in respective excitation frequency, and (ii) technical differences in the respective post-processing algorithm for stiffness map reconstruction of the imaging modalities.

With respect to technical difference in excitation frequency, let us consider the following. An external driver used in MRE produces harmonic waves with a narrow frequency bandwidth, which means that the wave energy can be concentrated at a desired frequency (e.g., ~60 Hz for liver). UE methods, on the other hand, use high-intensity short-duration ultrasound "push" pulses to generate a shear wave with a wide frequency spectrum. Although it is possible to filter out the desired shear wave frequency in UE to make it comparable to the one in MRE at the post-processing stage, it is difficult to control how the energy of the wave is distributed within that spectrum at the excitation step. The difference in the frequency content of the produced waves in these methods (single frequency vs. multi-frequency excitation) causes the shear-wave group velocity in UE to be different from, and thus not match that of MRE.

With respect to technical difference in the post-processing algorithm for stiffness map reconstruction, let us further consider the following. In MRE, a local frequency estimation (LFE) algorithm is typically used for stiffness map reconstruction. LFE calculates the shear wave speed by estimating the local spatial frequency of the shear wave propagation pattern through an algorithm that combines local estimates of instantaneous frequency over several scales. However, in UE, an inverse wave equation or 2D cross-correlation algorithm is used. Additionally, the reconstructed stiffness map in UE is 2D, while the reconstructed stiffness map is 3D in MRE.

Referring again to FIGS. 3 and 4, the figures further illustrate a shear modulus obtained by MRE and UE, respectively. As can be observed from the figures, the shear modulus (or stiffness) obtained by UE (FIG. 4) is higher than that of MRE (FIG. 3) for all liver fibrosis levels (F0 to F4). In further comparison, MRE has a higher success rate than UE in diagnosing liver fibrosis (93% vs. 82%). MRE has a more robust quantification performance due to its higher shear wave SNR, 3D volume imaging, and by assessing a larger proportion of the liver, which may reduce sampling variability.

However, compared to MRE, UE is less expensive, faster, highly portable, and widely available, and UE has been independently validated in numerous clinical institutions/facilities worldwide. There are also clinical care sites that do not have access to MRI scanners, and some patients prefer not to undergo MRE again due to being constrained in the MR scanner. In these cases, UE is preferred over MRE. Therefore, depending on the availability of the systems at clinical institutes, patient comfort level, and cost of care, MRE or UE is preferred for diagnosis and monitoring of liver fibrosis.

As was in the past, if a patient were to undergo an MRE/UE exam, then the monitoring of liver fibrosis at the follow-up measurements would have to remain MRE/UE (i.e., the same image modality) for consistency. However, MRE is expensive, and performing MRE measurements at several time points put a significant financial burden on the patient and perhaps discomfort. Direct comparison of UE and MRE measurements without appropriate knowledge can disadvantageously lead to misinterpretation. Another shortcoming of the modality-dependent stiffness cut-off values is that they only offer discrete staging or grading outcomes (e.g., grade 2 or 3). However, during the treatment, sometimes, it is also important to quantify the continuous stiffness value change caused by the therapy even within the same stage. The embodiments of the present disclosure advantageously offer a solution by enabling the utilization of UE and MRE at different time points interchangeably to help clinicians better quantify and monitor the progression/regression of liver fibrosis.

A second problem overcome by the embodiments of the present disclosure is bridging the gap between MRE and UE for the follow-up fibrosis monitoring and for removing a dependency on one image modality. The embodiments of the present disclosure provide a smart reporting system across both image modalities. In contrast, with respect to current clinical practice, depending on the type of the elastography exam performed (MRE or UE), a different lookup table is used to find the fibrosis level corresponding to the measured liver stiffness. Considering differences in the training level of ultrasound and MM technicians or users, it is not convenient for them to correlate the different stiffness levels at different time points using various imaging modalities. To address this problem, the embodiments of the present disclosure advantageously provide a smart report/dashboard having applicability across image modalities representing the fibrosis stage at all time-points and changes in stiffness values showing a trend from baseline to current exam. The dashboard presented by the embodiments of the present disclosure also advantageously removes a dependency on one image modality and helps users interpret changes in liver fibrosis easier, regardless of their expertise.

In particular, the embodiments of the present disclosure provide a solution to bridge the gap between MRE and UE stiffness results by bringing UE closer to MRE without the need to perform the MRE exam. According to one embodiment, a shear wave elastography system and method predict a corresponding MRE stiffness map (and/or stiffness value) and confidence level by only performing a UE measurement, and vice versa. In particular, the shear wave elastography system and method use the UE measured stiffness map as an input and applies artificial intelligence (AI) based algorithms to 1) predict the corresponding MRE stiffness map and 2) predict a confidence level on the obtained stiffness map (or a confidence score regarding the obtained stiffness value). Finally, the system and method provide a smart report/dashboard across image modalities (UE/MRE) showing the fibrosis stage at a plurality of time-points for a given patient, changes in stiffness values on a plot, and a table along with the measured and predicted stiffness maps.

As will be understood from the disclosure herein, the method and system according to the embodiments of the present disclosure can be divided into three aspects. In a first aspect, the method includes predicting a corresponding MRE stiffness value by only performing a UE measurement, and vice versa. In a second aspect, the method includes predicting a confidence score regarding the obtained stiffness value (e.g., an obtained liver stiffness value). Thirdly, the method includes providing a smart report showing the fibrosis stage and changes in stiffness value for a given patient over time.

Figure 2:
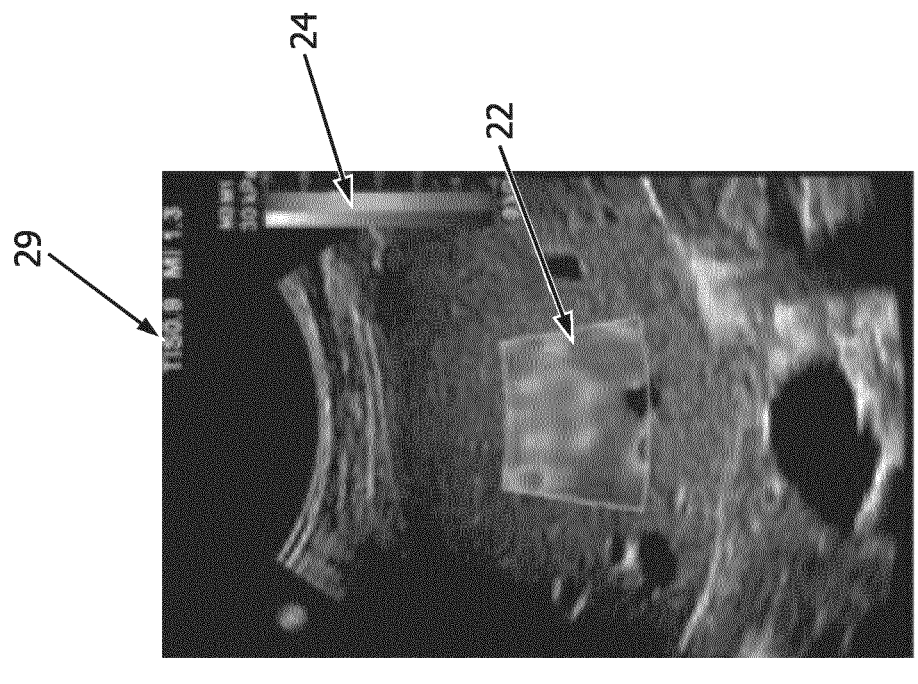
FIG. 2 is an illustrative flow-diagram view of a method for ultrasound shear wave elastography (UE)
Figure 2:
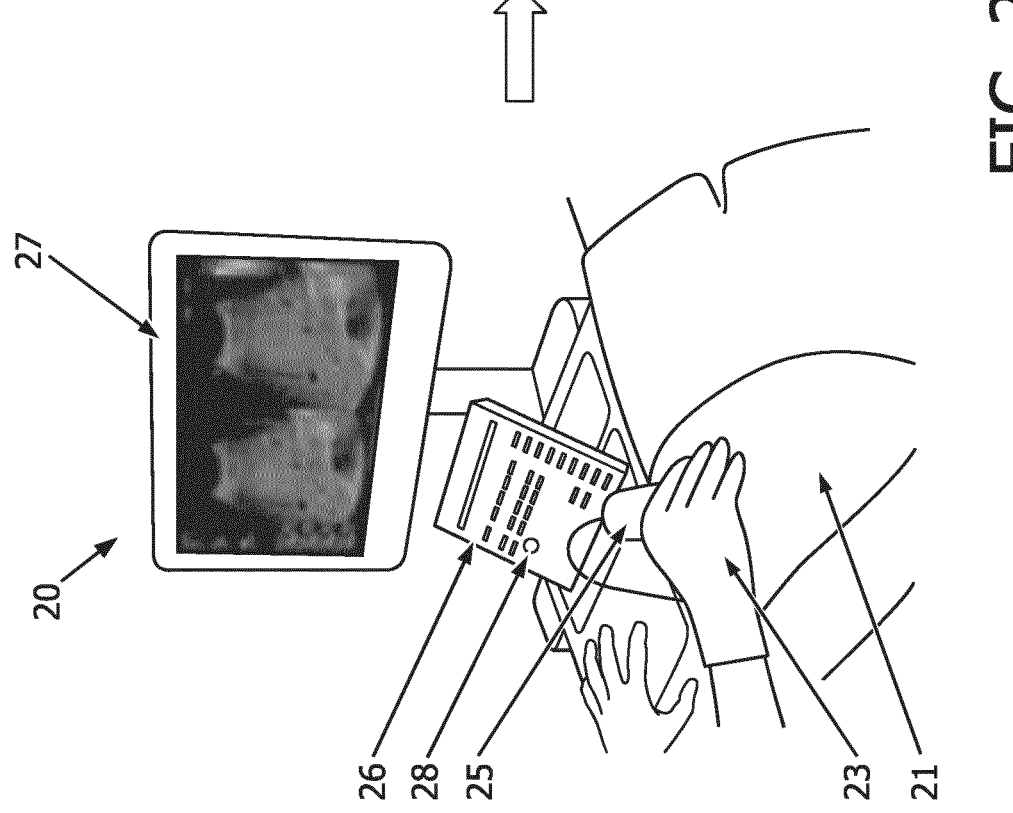
Figure 5:
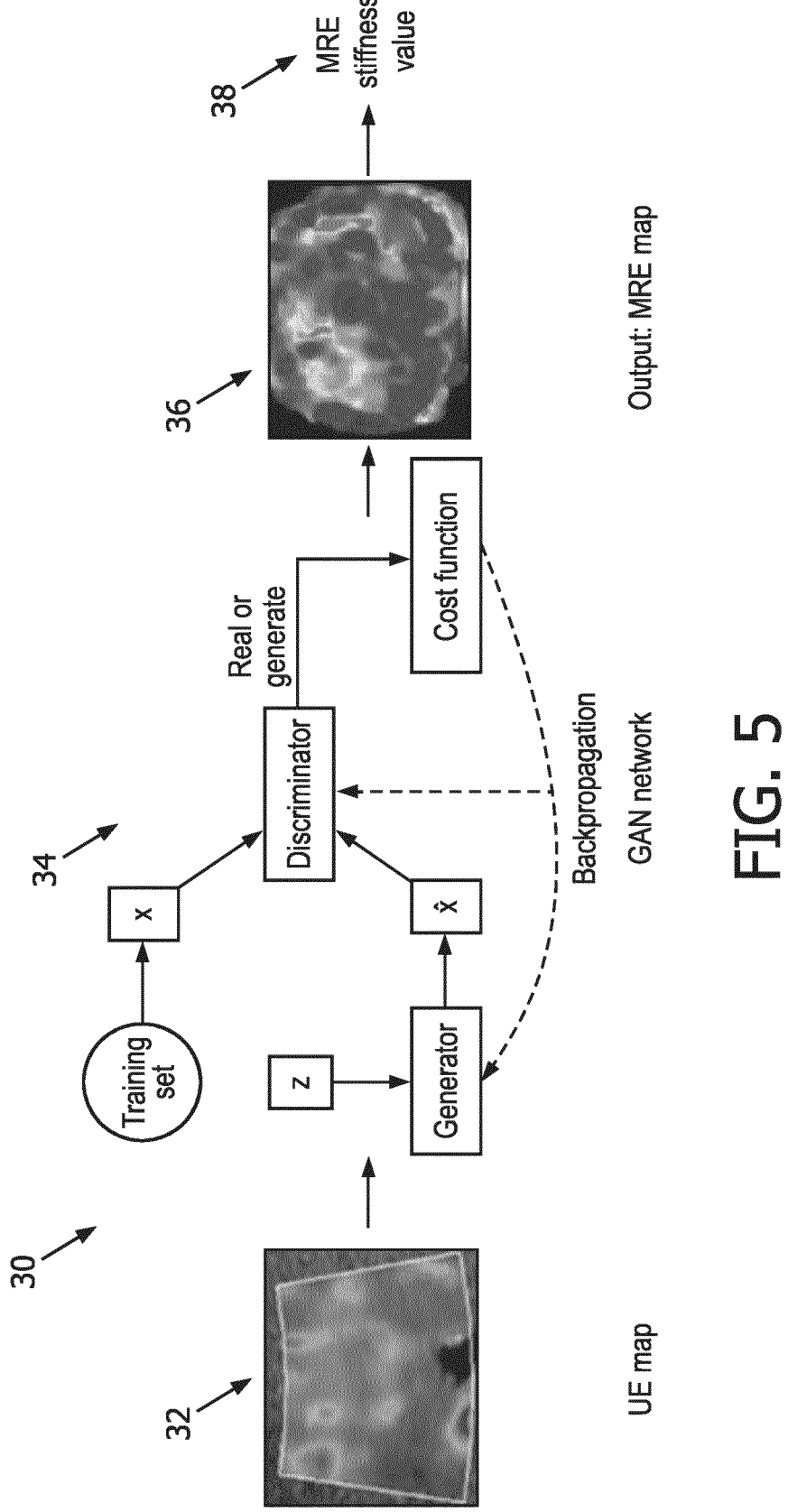
FIG. 5 is an illustrative flow-diagram view of a step of predicting a corresponding first imaging modality elastography value based only on an obtained or measured second imaging modality elastography value according to an embodiment of the present disclosure. Portions of the flow-diagram view are reproduced in FIGS. 5A, 5B and 5C for clarity.
Figure 5A:
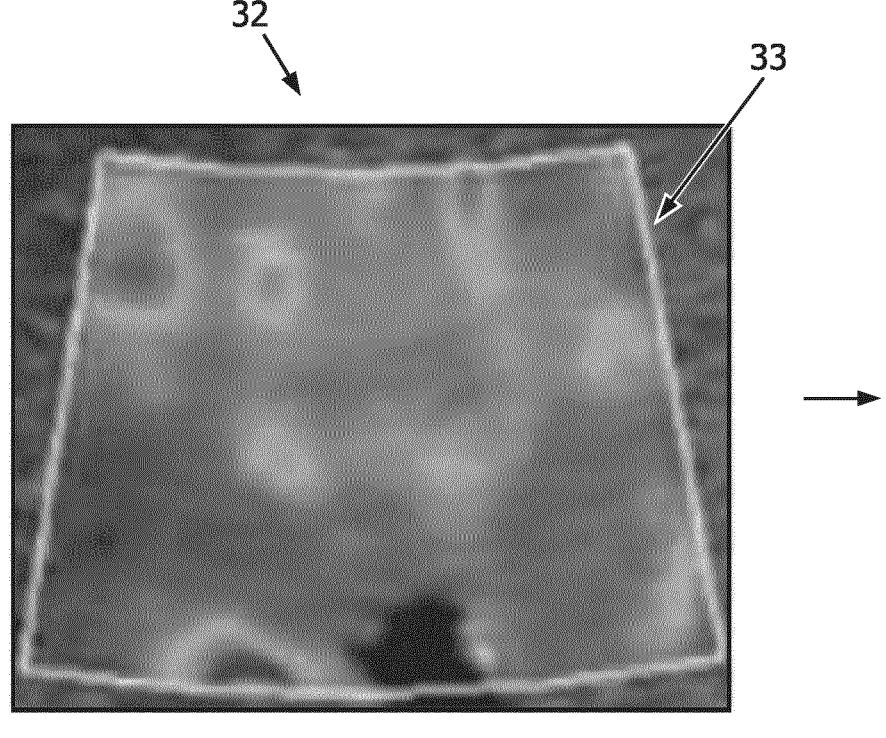

Turning now to FIG. 5, there is shown an illustrative flow-diagram view of a step of predicting a corresponding first imaging modality elastography value based only on the obtained second imaging modality elastography value, designated by reference numeral 30, according to an embodiment of the present disclosure. Portions of the flow-diagram view of FIG. 5 are reproduced in FIGS. 5A, 5B and 5C for clarity. With respect to predicting a corresponding MRE stiffness value, consider the following as an example. The method begins with performing an elastography measurement via a second imaging modality, different from a first imaging modality, to obtain at least one second imaging modality elastography value, designated by reference numeral 32, of a region of interest. In the present example, the second imaging modality is UE and the first imaging modality is MRE. With reference again to FIG. 2, an ultrasound UE measurement is performed for a given region of interest (ROI) of a patient 21 using the UE device 20. UE device 20 includes, for example, an ultrasound probe 25, a graphical user interface or ultrasound scanner touch panel 26, and a display 27. A system operator or user 23 may perform an ultrasound UE measurement for the region of interest, and the resulting measurement, such as stiffness map 22 and corresponding color-coded stiffness scale 24, is displayed as indicated by reference numeral 29 in FIG. 2 on display device 27. Subsequent to the UE measurement being obtained via the UE device 20, a soft button 28 is provided on the graphical user interface or ultrasound scanner touch panel 26 of the UE device. The soft button 28 may be labelled as "Obtain corresponding MRE stiffness map (or stiffness value)" or similar.

Upon a user selection of the soft button 28, the ultrasound scanner 20 launches a corresponding stiffness value prediction application, designated by reference numeral 34 in FIG. 5. The stiffness value prediction application comprises suitable program instructions for predicting, via a processor, at least one corresponding first imaging modality elastography value based only on the obtained second imaging modality elastography value. In one embodiment, the stiffness value prediction application is configured to implement a deep learning-based algorithm, such as generative adversarial network (GAN) or convolutional neural network (CNN).

Figure 5B:
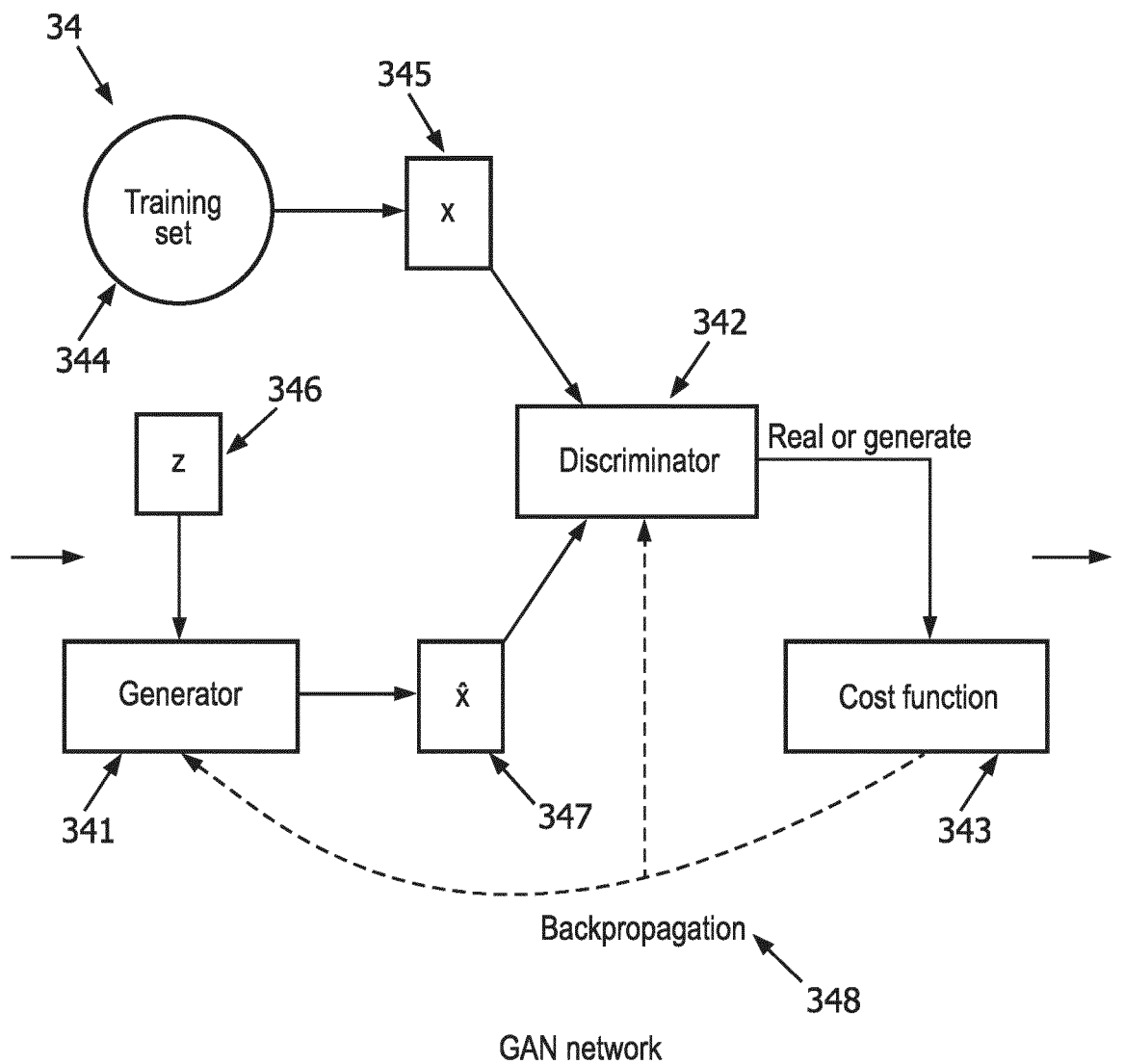
Figure 5C:
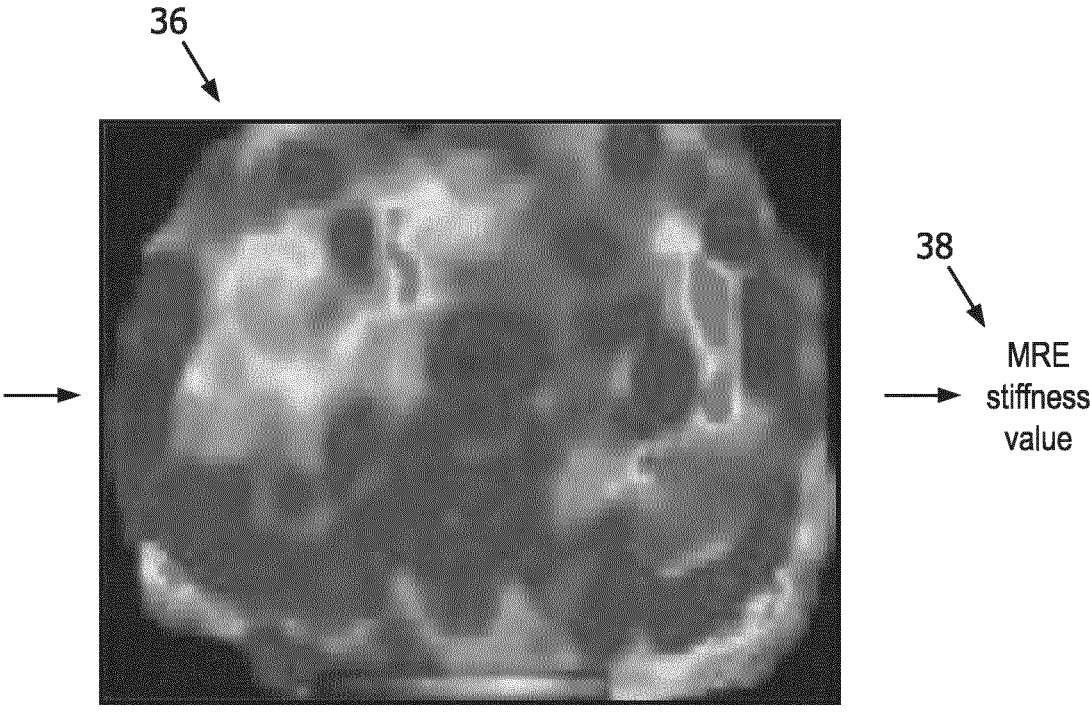

Deep learning is type of artificial neural network that tries to resemble the multi-layered human cognition system. GAN and CNN are example of deep learning-based algorithms known in the art and only briefly described herein. With reference now to FIG. 5B, the generative adversial network (GAN) 34 includes a deep learning architecture that contains two networks: a generator 341 and a discriminator 342. The generator and discriminator networks are trained jointly with a backpropagation algorithm, via cost function 343. The training makes the generative network 341 better at generating more realistic samples (e.g., real) and the discriminator network better at differentiating artificially generated samples (e.g., generate). According to the embodiments of the present disclosure, the deep learning-based algorithm is initiated to predict a corresponding MRE stiffness map 36 based only on an obtained UE stiffness map (or elastography value) 32. In addition, a training set 344 is input to the discriminator 342, via a processing block "x", as indicated via reference numeral 345. In operation, the obtained UE stiffness map 32, having a region of interest 33 (FIG. 5A), is input to generator 341 of the GAN network 34, via a processing block "z", indicated by reference numeral 346. The output of the generator 341 is input to the discriminator 342, via processing block "x-hat", indicated by reference numeral 347. The discriminator 342 may output the predicted MRE stiffness map 36 and/or a corresponding predicted average value of the MRE stiffness map (i.e., stiffness value) 38, as illustrated in FIG. 5C. In addition, the generator and discriminator networks are trained jointly with the backpropagation algorithm via a backpropagation output 348 of cost function 343. The predicted MRE stiffness map 36, and the corresponding predicted average value of the stiffness map 38 are then stored in a suitable memory (not shown) of the ultrasound scanner 20.

For training, the UE and MRE measurements may be performed on the same day in a group of patients with different levels of liver fibrosis as well as healthy controls. In the deep learning-based algorithm, the ultrasound UE and MRE stiffness maps are used as (i) input and (ii) the ground truth, respectively.

The training phase can be vendor-agnostic and not limited to one vendor's scanners. Additionally, since the MRE stiffness map is three dimensional (3D) (unlike UE), the UE stiffness map in the same plane should be fed into the GAN network 34 for consistency. To match the UE and MRE plane, a suitable navigation system is preferably used for guidance to ensure that the same MR plane is selected for UE measurements. During the UE measurements, the user or UE system operator 23 (FIG. 2) moves the ultrasound probe 25 (FIG. 2) using the UE system 20 (FIG. 2) until the user reaches the matching MR plane. Upon reaching the matching MR plane, the user 23 then starts acquisition of the stiffness measurements.

Figure 6:
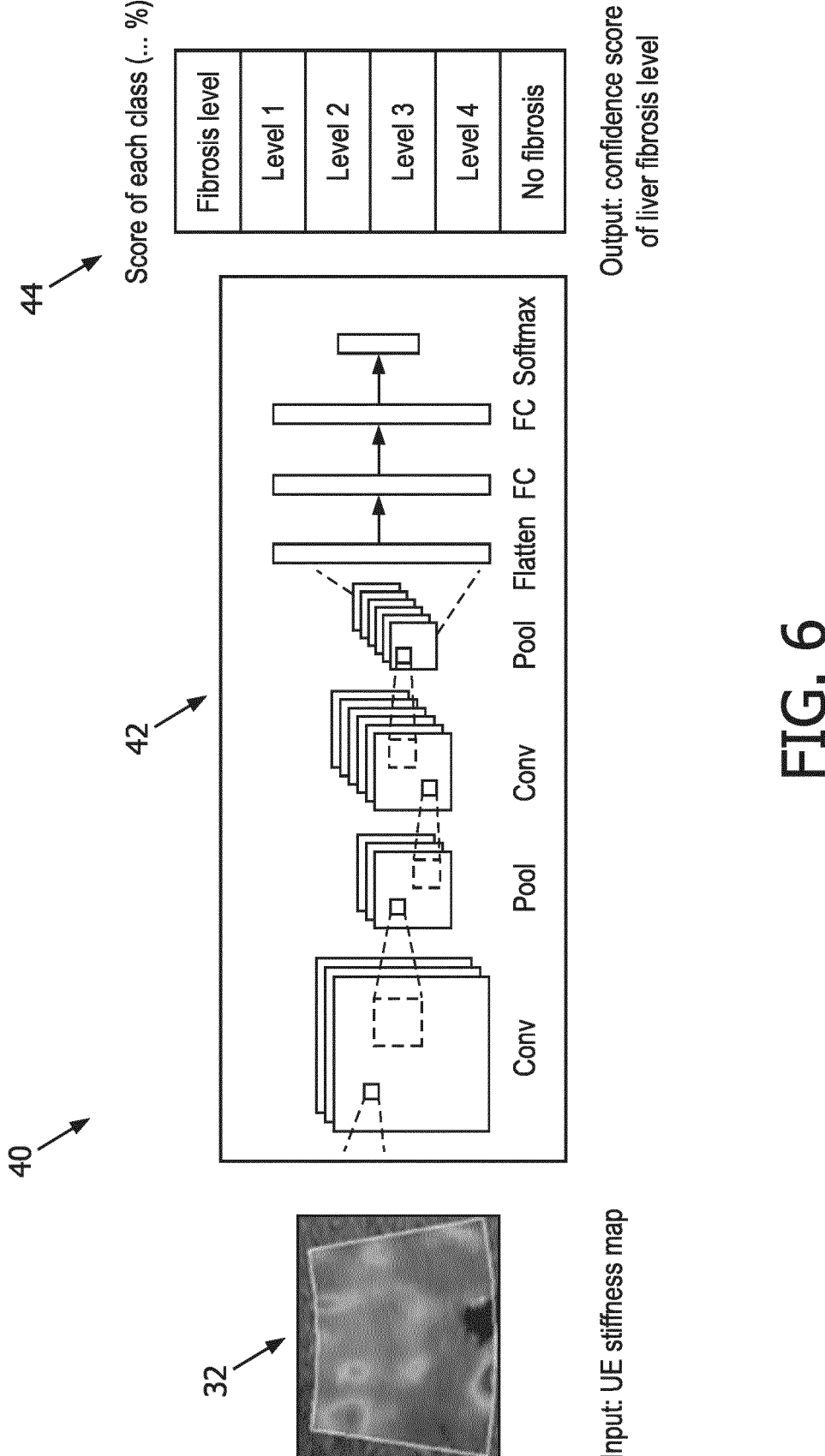
FIG. 6 is an illustrative flow-diagram view of a step of predicting a confidence score according to an embodiment of the present disclosure. Portions of the flow-diagram view are reproduced in FIGS. 6A, 6B and 6C for clarity, wherein the predicted confidence score relates to an elastography value obtained or measured via the second imaging modality.

With reference now to FIG. 6, there is shown an illustrative flow-diagram view of a step of predicting a confidence score, collectively indicated by reference numeral 40, according to an embodiment of the present disclosure, wherein the predicted confidence score relates to the elastography value obtained (i.e., actually measured elastography value) via the second imaging modality. Portions of the flow-diagram view are reproduced in FIGS. 6.1, 6B and 6C for clarity. The automatic confidence score on the obtained stiffness value is determined as discussed in the following. The application or function of automatically determining a confidence score on the obtained stiffness value, designated by reference numeral 42, is activated simultaneously with the deep learning-based application 34 (i.e., the deep learning-based algorithm) in the previous step discussed herein with reference to FIG. 5. The confidence score, designated by reference numeral 44, of the obtained or actual measured stiffness map is realized using deep learning-based algorithms such as convolutional neural network (CNN) to provide real-time classification (FIG. 6).

Figure 6A:
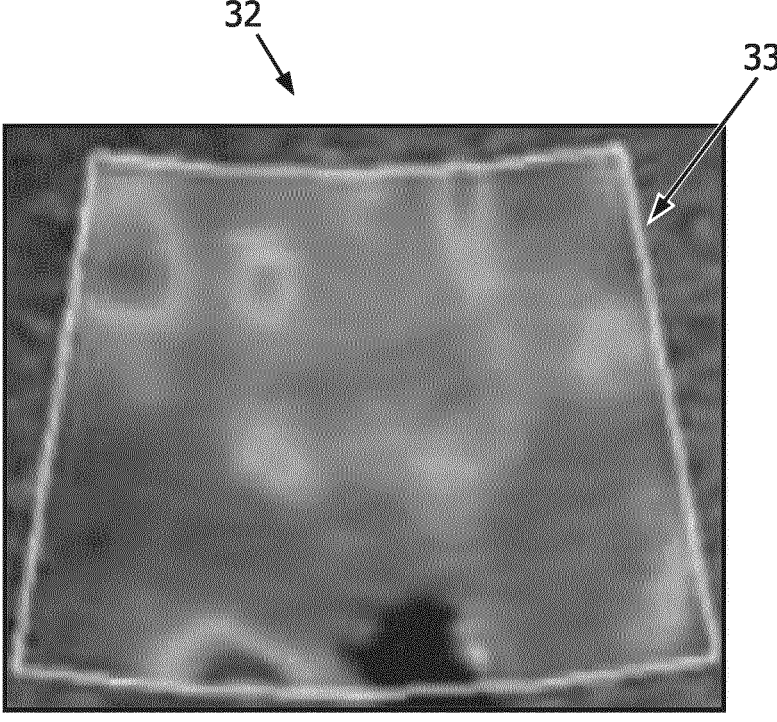
Figure 6B:
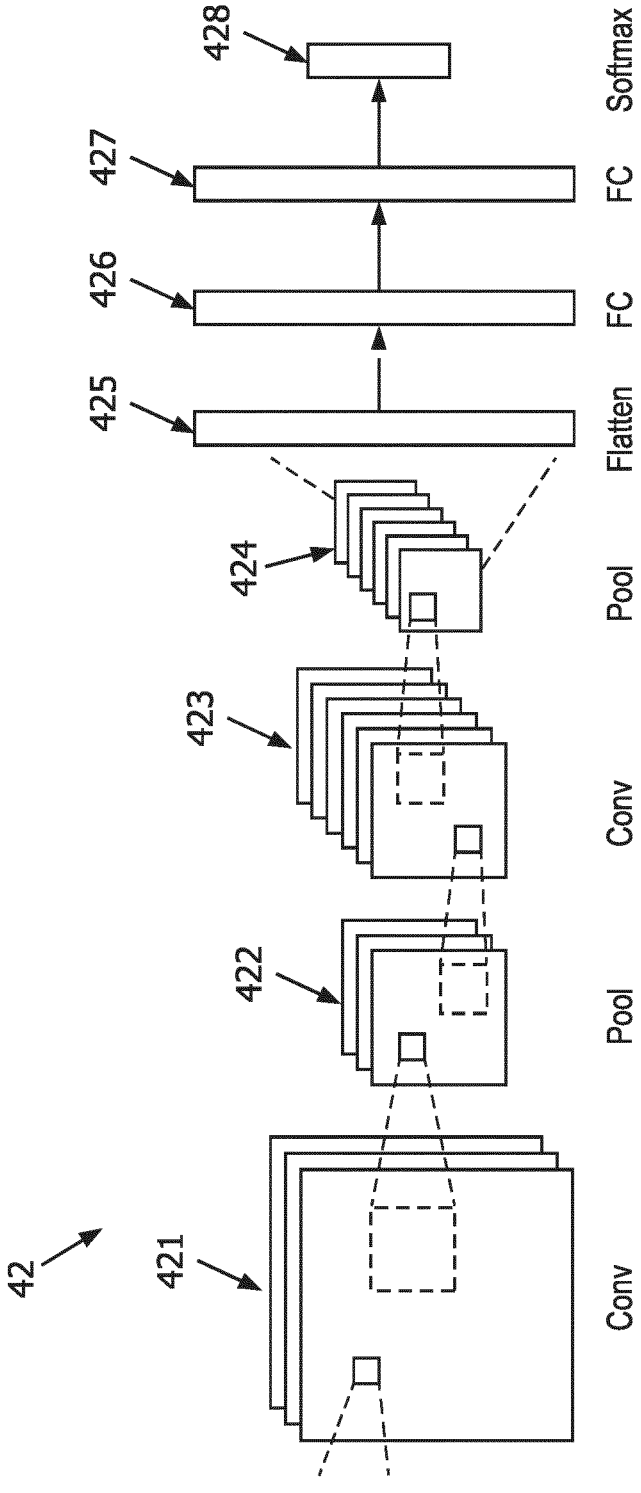

The convolutional neural network (CNN) includes a deep learning architecture and is used in medical imaging research due to an ability to preserve spatial relationships when filtering input images. Spatial relationships in medical imaging define tissue interfaces, structural boundaries, or joints between muscle and bone; and thus, CNNs have found special attention. A schematic diagram of a convolutional neural network 42 is shown in FIG. 6B. With reference to FIGS. 6, 6A and 6B, CNN 42 may take an input image of raw pixels (e.g., UE stiffness map 32) and transform it via convolutional layers (Cony) 421 and 423, rectified linear layers (Flatten) 425, and pooling layers (Pool) 422 and 424. This is then fed into a fully connected layer (FC) 426 and 427, which assigns probabilities or class scores to categorize the input (i.e., UE stiffness map 32) into the class with the highest probability (Softmax) 428. Pixels in an image can be processed by a different weight in a fully connected layer, or alternatively, every location can be processed using the same set of weights to extract various repeating patterns across the entire image. These trainable weights are referred to as kernels or filters; and are applied using a dot product or convolution and then processed by a nonlinearity function. Each convolutional layer may have several filters to extract multiple sets of patterns at each layer. Each convolutional layer (Cony) 421 and 423 is often followed by a pooling layer (Pool) 422 and 424, respectively, that reduces dimensionality and imposes translational invariance. These convolutional and pooling layers can be stacked together to form a multilayer network that often ends in one or more fully connected layers 426 and 427.

Figure 6C:
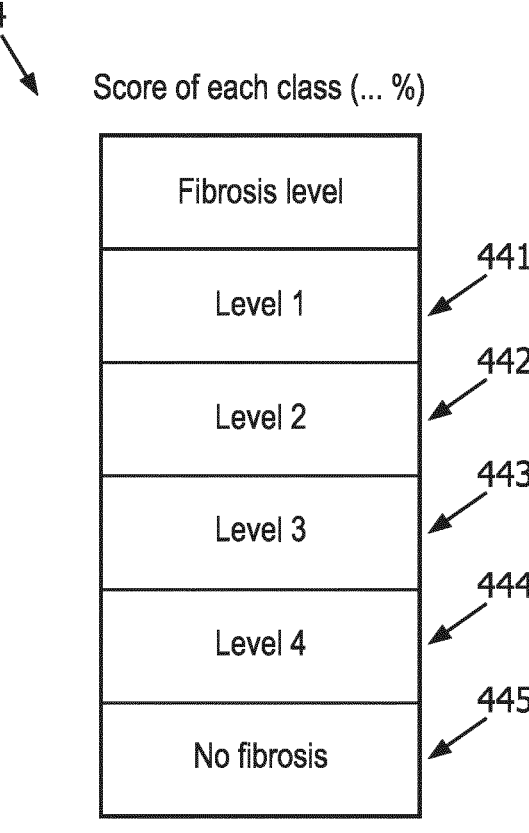
Figure 7:
FIG. 7 is an illustrative graphical user interface view of a smart report dashboard according to an embodiment of the present disclosure, in which FIG. 7 continues on a FIG. 7 continued sheet for clarity. In addition, portions of the flow-diagram view are reproduced in FIGS. 7A and 7B for clarity.
Figure 7:
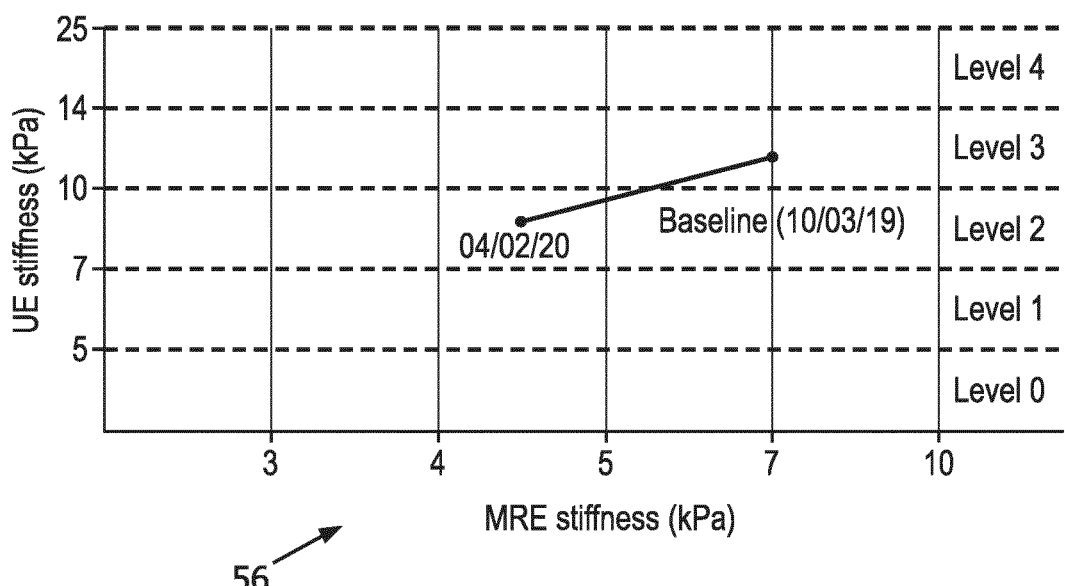
Figure 7:
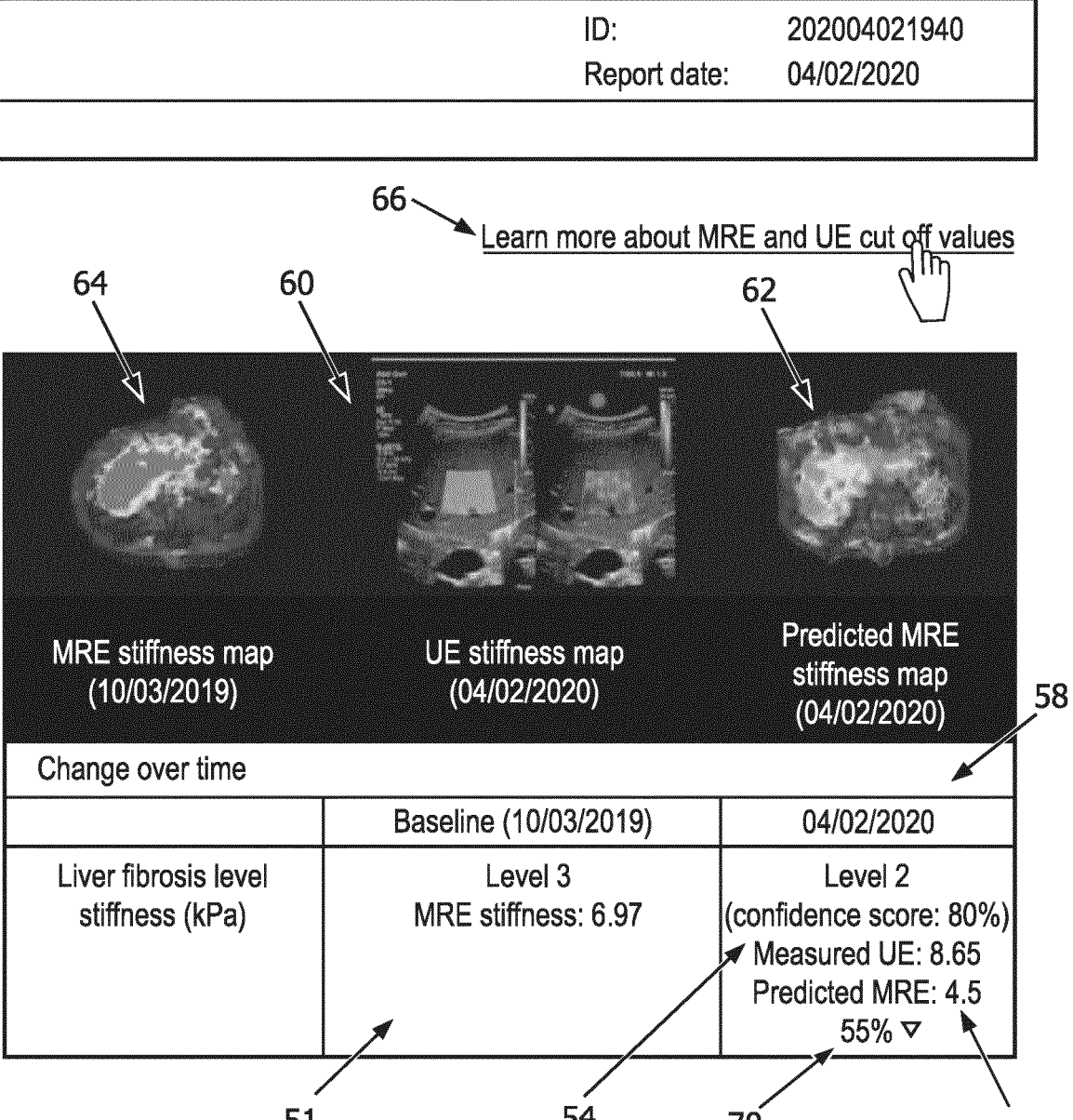

When the region of interest 33 (FIG. 6.1) comprises a patient's liver, the output of the deep learning-based algorithm is the liver fibrosis level with the highest confidence score 44 (FIG. 6C). In other words, probabilities or class scores for each class are assigned to categorize the input (e.g., elastography value 32) into respective fibrosis levels (Level 1, Level 2, Level 3, Level 4 and No fibrosis, designated by reference numerals 441, 442, 443, 444 and 445, respectively). The class with the highest probability, representative of the liver fibrosis level, is then output. For example, if the highest confidence score predicted by the AI model (i.e., the convolutional neural network (CNN) of FIG. 6) belongs to the fibrosis level 2 (e.g., the confidence score for level 2=0.82, for level 1=0.05, for level 3=0A0, for level 4=0.02, and no fibrosis=0.01), then the confidence score equals 82% and it means that we are 82% confident that the stiffness value measured by the second imaging modality (e.g., the UE modality) represents a level 2 fibrosis. The highest probability and corresponding fibrosis level are saved in a suitable memory (not shown) and output or shown via the GUI 26 or on a smart report dashboard 50, as will be discussed further herein with respect to FIG. 7. For example, once the confidence score (e.g., 44 in FIG. 6) and stiffness map (e.g., 36 in FIG. 5) are predicted, a "Smart report" soft button 28 is rendered or made to appear on the ultrasound scanner touch panel 26 so that a system user 23 may click on the soft button 28 for observing the final results, via the smart report dashboard 50 (FIG. 7). As used herein, fibrosis stage is understood to be the same as fibrosis level. In addition, predicted confidence level and predicted confidence score are used interchangeably herein, further being based on an actual measured elastography value, e.g., measured UE stiffness map.

In one embodiment, the predicted confidence score is related to the measured stiffness value in the second imaging modality. In particular, the predicted confidence score of the measured stiffness value in the second imaging modality indicates a level of confidence in the reported fibrosis level measured by the second imaging modality. The AI model for predicting the confidence score of the fibrosis level is calibrated/evaluated using liver biopsy as the ground truth in the training phase. In other words, with respect to the deep learning-based algorithm in the training phase, a UE stiffness map and liver biopsy are used as (i) input and (ii) ground truth, respectively. For training, the UE and liver biopsy may be performed on the same day in a group of patients with different levels of liver fibrosis. This training applies to the determination of the "confidence score".

Figure 7A:
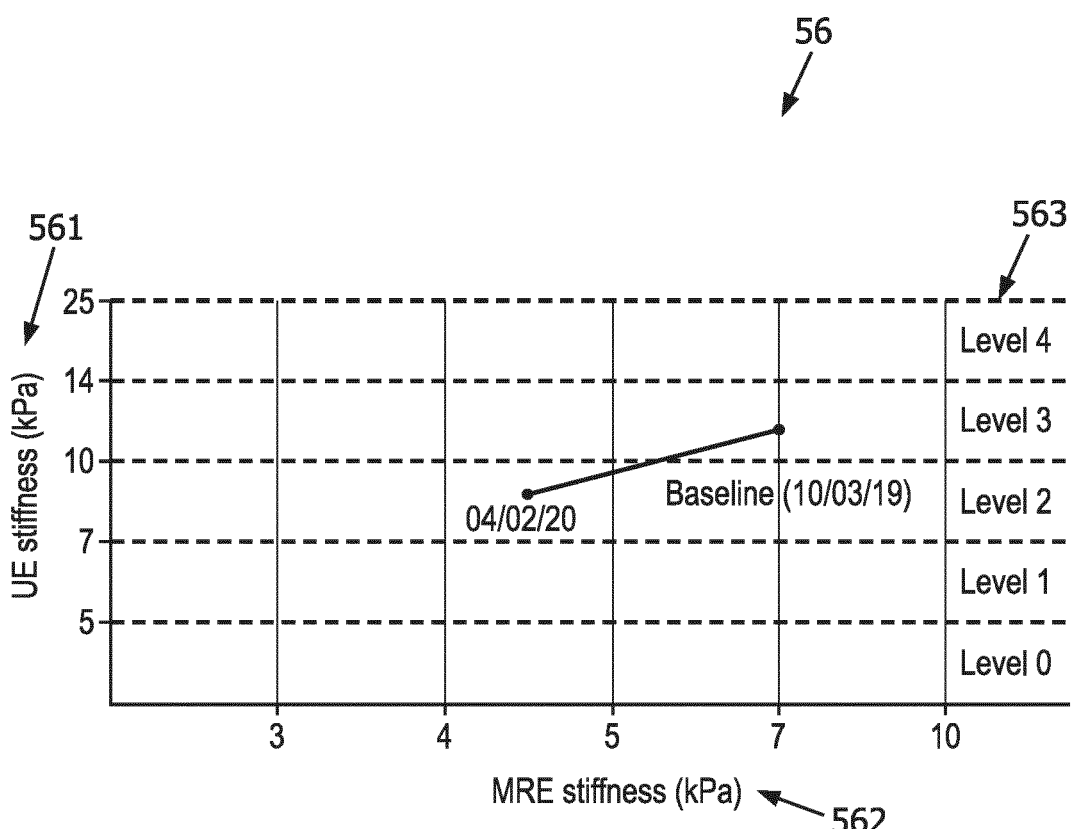

With reference now to FIG. 7, there is shown an illustrative graphical user interface view of a smart report dashboard, designated by reference numeral 50, according to an embodiment of the present disclosure. Portions of the flow-diagram view are reproduced in FIGS. 7A and 7B for clarity. The smart report dashboard 50 comprises a graphical user interface which may include one or more forms of multimedia. Considering the difference in the training level of ultrasound and MRI users, it is not convenient for them to correlate the different stiffness levels at different time points using various imaging modalities. The smart report or smart report dashboard 50 helps users better monitor fibrosis changes.

Figure 7B:
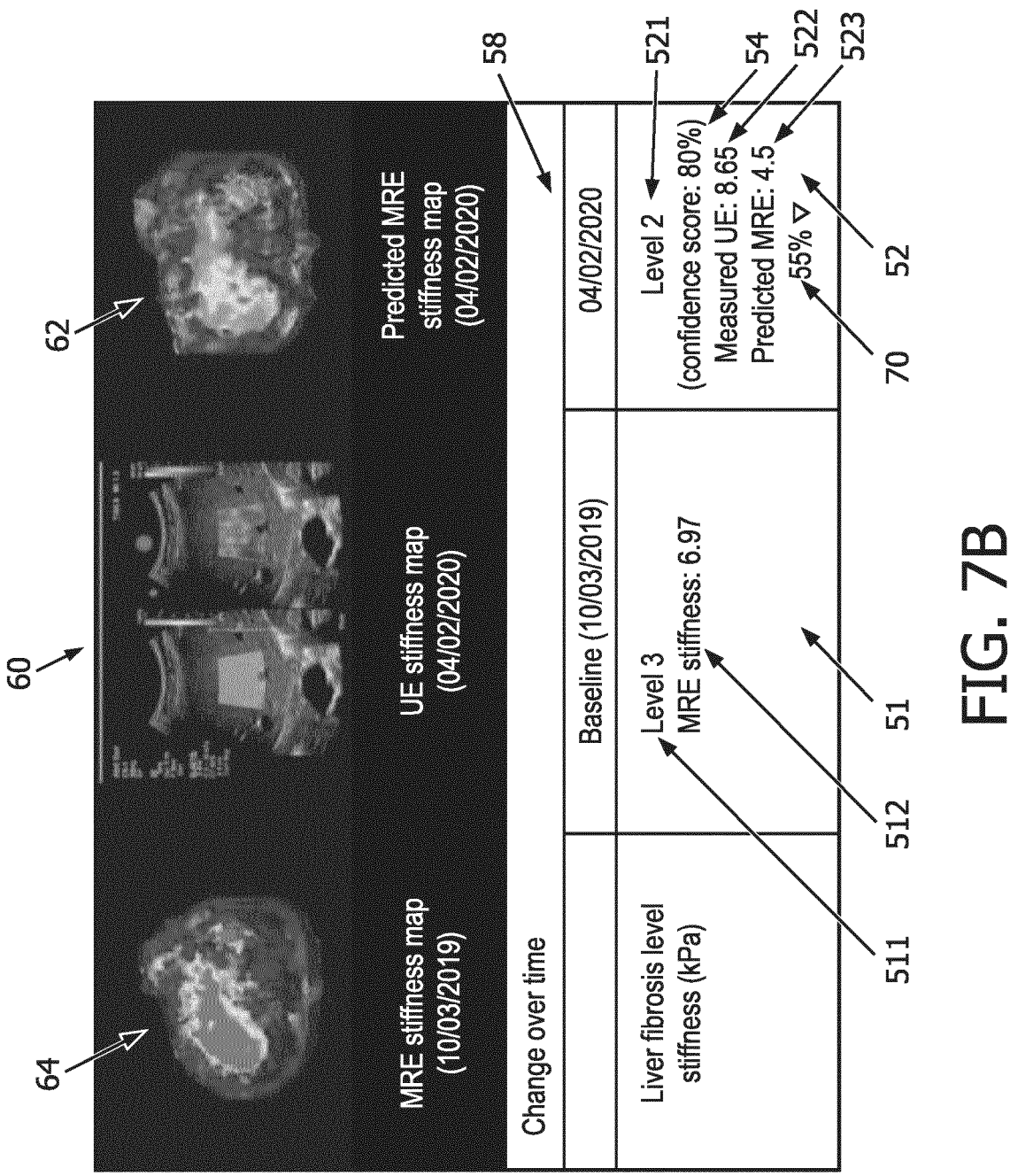

Upon the user clicking on "smart report" soft button 28 on the ultrasound scanner touch panel 26, a smart dashboard 50 will be automatically generated (FIG. 7) which includes showing one or more of the following. A current fibrosis stage or level, designated by reference numeral 52, and the corresponding predicted confidence score, designated by reference numeral 54, obtained in the previous step as discussed herein with reference to FIG. 6 is provided. In one embodiment, the current fibrosis stage 52 includes an indication of the fibrosis level 521, the elastography value 522 obtained via the second imaging modality elastography measurement (e.g., measured UE stiffness value), and the predicted elastography value 523 (e.g., predicted MRE stiffness value) corresponding to a first imaging modality elastography measurement based on the obtained second imaging modality elastography measurement. The obtaining of the elastography value 522 via the second imaging modality elastography measurement, and the predicting of the elastography value 523 corresponding to the first imaging modality measurement, are achieved as discussed herein with reference to at least FIG. 5, UE stiffness map 32, predicted MRE stiffness map 36, and predicted MRE stiffness value 38. In one embodiment, the new stiffness value (i.e., measured UE value 522 and/or corresponding predicted MRE value 523) may be automatically added to a plot, designated by reference numeral 56, and a table, designated by reference numeral 58 of existing stiffness values measured during past exams. The plot 56 and/or table 58 may advantageously provide a meaningful illustration of changes in liver stiffness over time. With reference now to FIG. 7.1, the plot 56 shows the obtained fibrosis levels in one or more previous exams. With respect to plot 56, the left-hand vertical scale 561 comprises a stiffness scale for the second imaging modality in units of kPa, the horizontal scale 562 comprises a stiffness scale the first imaging modality in units of kPa, and the right-hand vertical scale 563 comprises a scale of fibrosis levels, from Level 0 to Level 4. As illustrated in the example of plot 56, a decrease in fibrosis level from a baseline (10/03/19) measurement obtained via the first imaging modality to a subsequent measurement (04/02/20) obtained via the second imaging modality is observed, corresponding to a change is fibrosis level from Level 3 to Level 2. Referring still to FIG. 7B, table 58 further includes fibrosis stage 51 which includes an indication of the fibrosis level 511 and the elastography value 512 obtained via a baseline (10/03/2019) with a first imaging modality elastography measurement (e.g., measured MRE stiffness value). In FIGS. 7 and 7B, the smart dashboard 50 further shows measured and predicted stiffness maps, designated by reference numerals 60 and 62, respectively, obtained as discussed herein with reference to FIG. 5, along with the baseline stiffness map, designated by reference numeral 64. It is noted that the baseline stiffness map 64 is a previously obtained stiffness map, such as, at an initial fibrosis exam, obtained via one or more of the MRE or UE imaging modalities. A hyperlink, designated by reference numeral 66, is included in smart dashboard 50 for redirecting the user to more information about the MRE/UE cut-off values, e.g., guideline material (reference paper, etc.) regarding the differences between MRE/UE. In addition, the smart dashboard 50 provides findings, such as, an increase or decrease in fibrosis stiffness, which can be expressed as a finding field, designated by reference numeral 68, and/or via a suitable symbolic representation (e.g., a percentage number and graphic, the graphic pointing up for an increase or down for a decrease), designated by reference numeral 70. As shown in FIG. 7, the smart report dashboard 50 shows stiffness values, changes in liver fibrosis levels on a plot and table, the measured and predicted stiffness maps, and a confidence score.

As should be understood herein, the stiffness map can be predicted in either direction. There are clinical sites that do not have access to MRI scanners, or some patients prefer not to undergo MRE due to being constrained in the MR scanner. In these cases, UE is preferred over MRE during the fibrosis diagnosis phase. However, during the treatment phase, to more accurately monitor liver fibrosis, MRE may be recommended because it has a higher success rate and more robust quantification performance compared to UE due to its higher shear wave SNR, 3D volume imaging and assessing a larger proportion of the liver. Therefore, there are cases where the patient undergoes a UE exam in the fibrosis diagnosis exam and MRE exam in a longitudinal follow-up measurement. In this scenario, the step of predicting an MRE stiffness map according to one embodiment of the present disclosure can be replaced by predicting a UE stiffness map and stiffness value based on the measured MRE stiffness map. The same deep learning-based algorithm and training process can be used, except that in this instance, the (i) input and (ii) ground truth will be MRE and UE stiffness maps, respectively.

Figure 8:
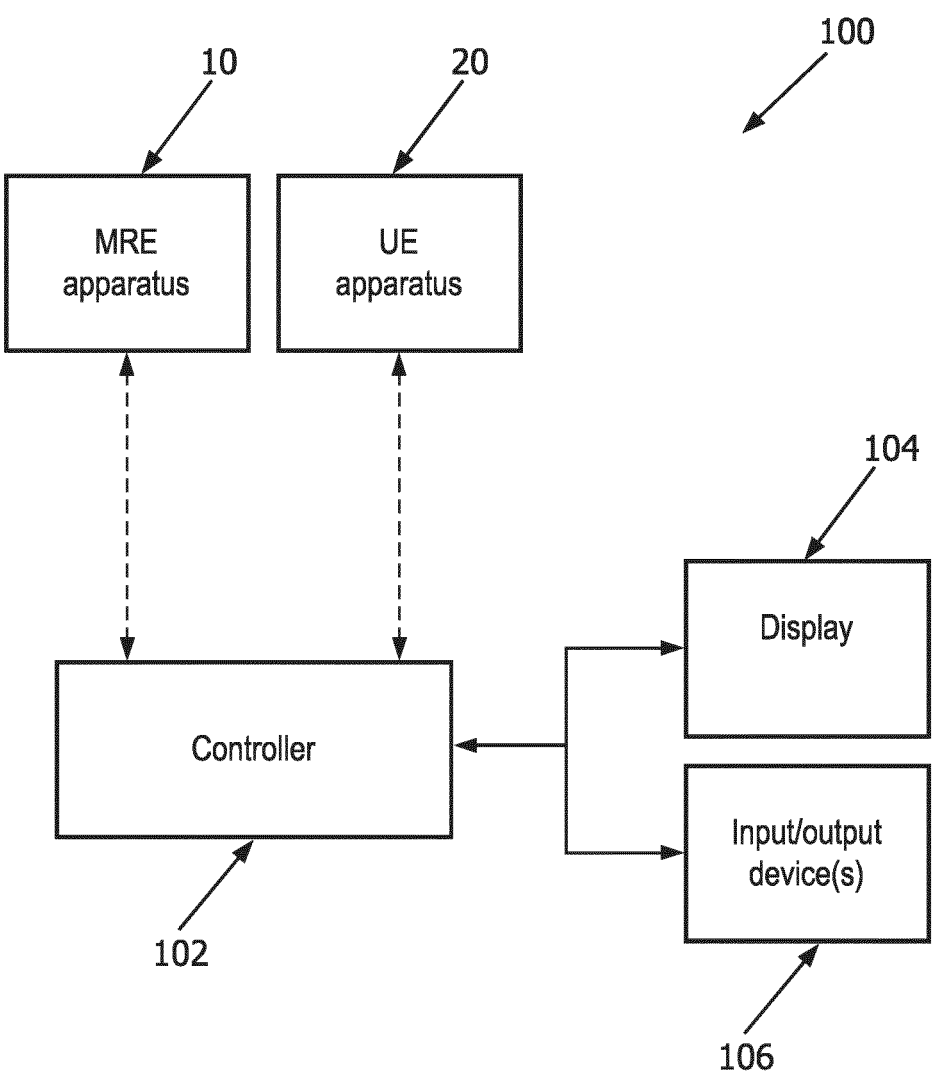
FIG. 8 is a block diagram view of a system for augmented interpretation of shear wave elastography between first and second imaging modalities according to an embodiment of the present disclosure.

With reference now to FIG. 8, there is shown a block diagram view of a system 100 for augmented interpretation of shear wave elastography between first and second imaging modalities according to an embodiment of the present disclosure. In this embodiment, the system 100 comprises at least a controller 102, a display 104, and input/output device(s) 106. Controller 102 is operatively coupled to one or more shear wave imaging modality system or apparatus, for example, the MRE system/apparatus 10 and/or the UE system/apparatus 20, according to the requirements of a given shear wave elastography implementation. In one embodiment, controller 102 comprises one or more of a microprocessor, microcontroller, field programmable gate array (FPGA), integrated circuit, discrete analog or digital circuit components, hardware, software, firmware, or any combination thereof, for performing various functions as discussed herein, further according to the requirements of a given shear wave elastography implementation and/or application. Controller 102 can further comprise one or more of various modules, units, or subsystems. In one embodiment, controller 102 can include system electronics comprising one or more of various modules, units, or subsystems, power source, and memory, as appropriate according to the requirements of the given shear wave elastography system implementation and/or application. In one embodiment, display 104 is operatively coupled to the controller 102 for displaying one or more soft button (e.g., soft button 28 as discussed herein), and the smart report dashboard 50 or one or more portions thereof (e.g., current fibrosis stage, confidence score, plot of stiffness values, table showing changes in stiffness over time, obtained and predicted stiffness maps, stiffness value, increase or decrease in fibrosis stiffness, etc.), according to the requirements of a given shear wave elastography system implementation. Input/output device(s) 106 can comprise one or more of an input/output device, user interface, tactile output device, touch screen, optical display, microphone, keypad, keyboard, pointing device, image capture device, video camera, audio output device, and any combination thereof, according to the requirements of a given shear wave elastography system implementation.

As discussed herein, various aspects of the embodiments of the present disclosure involve user interface components, for example, with an elastography feature that predicts the corresponding MRE stiffness map using UE (or vice versa, i.e., predicts the UE stiffness map using MRE). The embodiments of the present disclosure can be incorporated into a novel feature of ultrasound/MR scanners, i.e., included in the ultrasound (US) or magnetic resonance imaging (MM) scanner apparatus. Additionally, the smart reporting system/dashboard or graphical user interface and its features presented herein can be incorporated into ultrasound/MR scanners.

Accordingly, the embodiments of the present disclosure remove the need for keeping the same image modality for follow-up stiffness measurements to monitor the progression of liver fibrosis. Enabling UE instead of MRE for the follow-up stiffness measurements advantageously contributes to a lower cost of care for the patient. Additionally, the smart dashboard/report according to the embodiments of the present disclosure advantageously removes the dependency on one image modality in the reporting system. The method and system apparatus of the present disclosure further advantageously enables users with different levels of training/background to be able to monitor changes in liver fibrosis.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used by performing a baseline shear wave elastography measurement in both MRE and UE imaging modalities, and subsequently, performing one or the other of MRE or UE based on (i) an availability of a given shear wave elastography imaging modality at a subsequent point in time and (ii) a confidence score. At the subsequent point in time, either MRE or UE could be selected based on an acceptability of the confidence score for a respective predicted imaging modality elastography value, as discussed herein. If the confidence score was determined unacceptable for one imaging modality, or not within a given acceptable range, then the other imaging modality could be selected, i.e., based upon the confidence score being used as criteria to help make the choice between MRE and UE. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

What is claimed is:

1. A method for augmented interpretation of shear wave elastography between first and second imaging modalities, the method comprising:

performing an elastography measurement via a second imaging modality, different from a first imaging modality, to obtain at least one second imaging modality elastography value of a region of interest;

predicting, via a processor, at least one corresponding first imaging modality elastography value based on the obtained second imaging modality elastography value; and generating, via the processor and a display, a smart report dashboard that includes (i) a fibrosis level of the region of interest, wherein the fibrosis level is determined as a function of (i) (a) the at least one second imaging modality elastography value and/or (i) (b) the predicted at least one corresponding first imaging modality elastography value.

2. The method of claim 1, wherein the second imaging modality is selected between (i) magnetic resonance shear wave elastography (MRE) and (ii) ultrasound shear wave elastography (UE), and wherein the first imaging modality comprises the non-selected imaging modality of the second imaging modality.

3. The method of claim 1, wherein elastography values obtained via the second imaging modality are not comparable with elastography values obtained via the first imaging modality.

4. The method of claim 1, wherein the at least one second imaging modality elastography value and the at least one corresponding predicted first imaging modality elastography value each comprise one or more of (i) a stiffness map and (ii) a stiffness value in units of kPa.

5. The method of claim 1, further comprising:

predicting, via the processor, a confidence score related to the at least one second imaging modality elastography value, wherein the predicted confidence score comprises a highest percentage of confidence among percentages of confidence in each of multiple fibrosis levels F0-F4 based on the second imaging modality elastography measurement; and selecting, via the processor, a predicted fibrosis level based on the fibrosis level having the highest percentage of confidence.

6. The method of claim 1, wherein the smart report dashboard further includes (ii) a baseline fibrosis level of the region of interest, the baseline fibrosis level having been determined based on a baseline elastography measurement performed via the first imaging modality to obtain at least one baseline first imaging modality elastography value of the region of interest, the baseline elastography measurement having been performed prior to the elastography measurement via the second imaging modality.

7. The method of claim 6, wherein the smart report dashboard further includes (iii) a percentage change in elastography value between (iii)(a) the predicted at least one first imaging modality elastography value based on the obtained at least one second imaging modality elastography value and (iii)(b) the at least one baseline first imaging modality elastography value.

8. The method of claim 7, wherein the smart report dashboard further includes (iv) the at least one second imaging modality elastography value of the region of interest, (v) the predicted at least one corresponding first imaging modality elastography value of the region of interest, and (vi) a confidence score related to the at least one second imaging modality elastography value, wherein the confidence score is a percentage between 0 and 100 percent and is representative of a level of confidence in the fibrosis level that is based on the at least one second imaging modality elastography value.

9. The method of claim 1, wherein predicting the at least one corresponding first imaging modality elastography value comprises initiating a deep learning-based algorithm to predict the at least one corresponding first imaging modality elastography value, wherein the deep learning-based algorithm comprises one selected from the group consisting of a generative adversarial network (GAN) and a convolutional neural network (CNN).

10. The method of claim 9, further comprising:

determining, via the processor and a second deep learning-based algorithm, a confidence score related to the at least one second imaging modality elastography value, and wherein determining of the confidence score is automatically activated simultaneously with the initiating of the deep learning-based algorithm, the confidence score further for providing a real-time classification of, or a level of confidence in, the fibrosis level that is based on the at least one second imaging modality elastography value.

11. A system for augmented interpretation of shear wave elastography between first and second imaging modalities, comprising:

an input for receiving imaging data pertaining to an elastography measurement obtained from a second imaging modality;

a controller configured to perform an elastography measurement via the second imaging modality, different from a first imaging modality, to obtain at least one second imaging modality elastography value of a region of interest, predict at least one corresponding first imaging modality elastography value based on the obtained second imaging modality elastography value, and generate a smart report dashboard that includes (i) a fibrosis level of the region of interest, wherein the fibrosis level is determined as a function of (i)(a) the at least one second imaging modality elastography value and/or (i)(b) the predicted at least one corresponding first imaging modality elastography value; and a display in communication with the controller to display the smart report dashboard.

12. The system of claim 11, wherein the second imaging modality is selected between (i) magnetic resonance shear wave elastography (MRE) and (ii) ultrasound shear wave elastography (UE), and wherein the first imaging modality comprises the non-selected imaging modality of the second imaging modality.

13. The system of claim 11, wherein elastography values obtained via the second imaging modality are not comparable with elastography values obtained via the first imaging modality.

14. The system of claim 11, wherein the at least one second imaging modality elastography value and the at least one corresponding predicted first imaging modality elastography value each comprise one or more of (i) a stiffness map and (ii) a stiffness value in units of kPa.

15. The system of claim 11, wherein the controller is further configured to:

predict a confidence score related to the at least one second imaging modality elastography value, wherein the predicted confidence score comprises a highest percentage of confidence among percentages of confidence in each of multiple fibrosis levels F0-F4 based on the second imaging modality elastography measurement; and select a predicted fibrosis level based on the fibrosis level having the highest percentage of confidence.

16. The system of claim 11, wherein the smart report dashboard further includes (ii) a baseline fibrosis level of the region of interest, the baseline fibrosis level having been determined based on a baseline elastography measurement performed via the first imaging modality to obtain at least one baseline first imaging modality elastography value of the region of interest, the baseline elastography measurement having been performed prior to the elastography measurement via the second imaging modality.

17. The system of claim 16, wherein the smart report dashboard further includes (iii) a percentage change in elastography value between (iii)(a) the predicted at least one first imaging modality elastography value based on the obtained at least one second imaging modality elastography value and (iii)(b) the at least one baseline first imaging modality elastography value.

18. The system of claim 17, wherein the smart report dashboard further includes (iv) the at least one second imaging modality elastography value of the region of interest, (v) the predicted at least one corresponding first imaging modality elastography value of the region of interest, and (vi) a confidence score related to the at least one second imaging modality elastography value, wherein the confidence score is a percentage between 0 and 100 percent and is representative of a level of confidence in the fibrosis level that is based on the at least one second imaging modality elastography value.

19. The system of claim 11, wherein predicting the at least one corresponding first imaging modality elastography value comprises initiating a deep learning-based algorithm to predict the at least one corresponding first imaging modality elastography value, wherein the deep learning-based algorithm comprises one selected from the group consisting of a generative adversarial network (GAN) and a convolutional neural network (CNN).

20. The system of claim 18, wherein the processor is further configured to:

determine a confidence score related to the at least one second imaging modality elastography value, and wherein determining of the confidence score is automatically activated simultaneously with the initiating of a deep learning-based algorithm, the confidence score further for providing a real-time classification of, or a level of confidence in, the fibrosis level that is based on the at least one second imaging modality elastography value.

* * * * *